(12) United States Patent
Gewehr et al.

(10) Patent No.: US 7,598,206 B2
(45) Date of Patent: Oct. 6, 2009

(54) FUNGICIDAL MIXTURES

(75) Inventors: Markus Gewehr, Kastellaun (DE);
Reinhard Stierl, Freinsheim (DE);
Matthias Niedenbrück, Limburgerhof (DE); Udo Hünger, Lambsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/793,899

(22) PCT Filed: Dec. 21, 2005

(86) PCT No.: PCT/EP2005/013815

§ 371 (c)(1),
(2), (4) Date: Jun. 21, 2007

(87) PCT Pub. No.: WO2006/069715

PCT Pub. Date: Jul. 6, 2006

(65) Prior Publication Data

US 2008/0045414 A1 Feb. 21, 2008

(30) Foreign Application Priority Data

Dec. 23, 2004 (DE) .................. 10 2004 063 322

(51) Int. Cl.
*A01N 25/26* (2006.01)
(52) U.S. Cl. .................................... 504/100
(58) Field of Classification Search ............ 504/100, 504/101, 116
See application file for complete search history.

(56) References Cited

U.S. PATENT DOCUMENTS 6,313,147 B1 * 11/2001 Shaber et al. ............... 514/340

FOREIGN PATENT DOCUMENTS

EP   1 035 122   9/2000

WO   WO 2006/015728   2/2006

OTHER PUBLICATIONS

Hunter et al., Fungicidal Control of Botrytis cinera on Grape-vines in England, Plant Pathology, 27: 81-86, 1978.*
International Search Report for International Application No. PCT/EP2005/013815 with an International Filing Date of Jul. 5, 2007; Completion Date: Jun. 1, 2006; Date of Mailing Jun. 16, 2006.
International Preliminary Report on Patentability with Written Opinion of the International Searching Authority for International Application No. PCT/EP2005/013815 with an International Filing Date of Jul. 5, 2007.

* cited by examiner

*Primary Examiner*—Johann R Richter
*Assistant Examiner*—Kristie L Brooks
(74) *Attorney, Agent, or Firm*—Brinks Hofer Gilson & Lione

(57) ABSTRACT

Fungicidal mixtures, comprising as active components
1) the isoxazole derivative of the formula I,

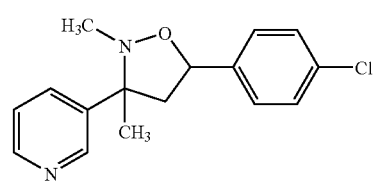

and
2) at least one active compound II selected from the group of the azoles, strobilurins, carboxamides, heterocyclic compounds, carbamates, guanidines, antibiotics, nitrophenyl derivatives, sulfur-containing heterocyclyl compounds, organometallic compounds, organophosphorus compounds, organochlorine compounds, inorganic active compounds, cyflufenamid, cymoxanil, dimethirimol, ethirimol, furalaxyl, metrafenone and spiroxamine,
in a synergistically effective amount, methods for controlling harmful fungi using mixtures of the compound I with active compounds II, the use of the compound I with active compounds II for preparing such mixtures and compositions comprising these mixtures.

19 Claims, No Drawings

FUNGICIDAL MIXTURES

The present invention relates to fungicidal mixtures comprising, as active components,
1) the isoxazole derivative of the formula I,

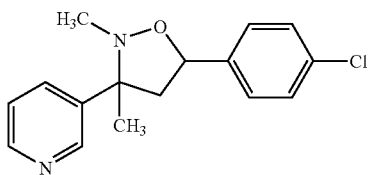

and
2) at least one active compound II selected from the following groups:
A) azoles, such as bitertanol, bromuconazole, cyproconazole, difenoconazole, diniconazole, enilconazol, epoxiconazole, fluquinconazole, fenbuconazole, flusilazole, flutriafol, hexaconazole, imibenconazole, ipconazole, metconazole, myclobutanil; penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole, hymexazole,
B) strobilurins, such as azoxystrobin, dimoxystrobin, enestroburin, fluoxastrobin, kresoxim-methyl, metominostrobin, orysastrobin, picoxystrobin, pyraclostrobin, trifloxystrobin;
C) carboxamides, such as carboxin, benalaxyl, boscalid, fenhexamid, flutolanil, furametpyr, mepronil, metalaxyl, mefenoxam, ofurace, oxadixyl, oxycarboxin, penthiopyrad, thifluzamide, tiadinil,
3,4-dichloro-N-(2-cyanophenyl)isothiazole-5-carboxamide, dimethomorph, flumorph,
flumetover, fluopicolide (picobenzamid), zoxamide, carpropamid, diclocymet, mandipropamid,
N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)prop-2-ynyloxy]-3-methoxyphenyl}ethyl-2-ethanesulfonylamino-3-methylbutyramide,
amides of the formula III,

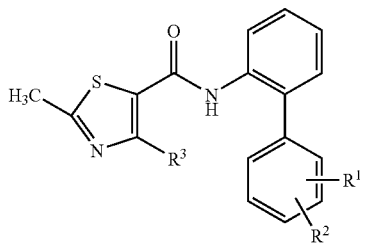

in which the variables and the index are as defined below:
$R^1$ and $R^2$ independently of one another are hydrogen, halogen, $C_1$-$C_6$-alkyl or $C_1$-$C_6$ haloalkyl, cyano, nitro, methoxy or trifluoromethoxy, with the proviso, that $R^1$ and $R^2$ are not simultaneously hydrogen, and $R^3$ is $CF_3$ or $CHF_2$;

D) heterocyclic compounds, such as fluazinam, pyrifenox, bupirimate, cyprodinil, fenarimol, ferimzone, mepanipyrim, nuarimol,
pyrimethanil,
triforine,
fenpiclonil, fludioxonil,
aldimorph, dodemorph, fenpropimorph, tridemorph, fenpropidin,
iprodione, procymidone, vinclozolin,
famoxadone, fenamidone, octhilinone, probenazole,
5-chloro-7-(4-methylpiperidin-1-yl)-6-(2,4,6-trifluorophenyl)-[1,2,4]triazolo[1,5-a]pyrimidine,
anilazine, diclomezine, pyroquilon, proquinazid, tricyclazole,
2-butoxy-6-iodo-3-propylchromen-4-one
acibenzolar-5-methyl, captafol, captan, dazomet, folpet, fenoxanil, quinoxyfen, or
N,N-dimethyl-3-(3-bromo-6-fluoro-2-methylindole-1-sulfonyl)-[1,2,4]triazole-1-sulfonamide;
E) carbamates, such as mancozeb, maneb, metam, metiram, ferbam,
propineb, thiram, zineb, ziram,
diethofencarb, iprovalicarb, flubenthiavalicarb, propamocarb,
methyl 3-(4-chlorophenyl)-3-(2-isopropoxycarbonylamino-3-methylbutyrylamino)propanoate,
methyl {2-chloro-5-[1-(3-methylbenzyloxyimino)ethyl]benzyl}-carbamate, methyl {2-chloro-5-[1-(6-methylpyridin-2-ylmethoxyimino)ethyl]-benzyl}-carbamate;
F) other fungicides, selected from the group consisting of guanidines: dodine, iminoctadine, guazatine,
antibiotics: kasugamycin, streptomycin, polyoxine, validamycin A,
nitrophenyl derivatives: binapacryl, dinocap, dinobuton,
sulfur-containing heterocyclyl compounds: dithianon, isoprothiolane,
organometallic compounds: fentin salts, such as fentin acetate,
organophosphorus compounds: edifenphos, iprobenfos, fosetyl, fosetyl aluminum, phosphorous acid and its salts, pyrazophos, tolclofos-methyl,
organochlorine compounds: chlorothalonil, dichlofluanid, flusulfamide, hexachlorobenzene, phthalide, pencycuron, quintozene, thiophanatemethyl, tolylfluanid,
inorganic active compounds: Bordeaux mixture, copper acetate, copper hydroxide, copper oxychloride, basic copper sulfate, sulfur,
others: cyflufenamid, cymoxanil, dimethirimol, ethirimol, furalaxyl, metrafenone, spiroxamine, in a synergistically effective amount.

Moreover, the invention relates to a method for controlling harmful fungi using mixtures of the compound I with active compounds II, to the use of the compound I with active compounds II for preparing such mixtures and to compositions comprising these mixtures.

The isoxazole derivative of the formula I, referred to above as component 1, its preparation and its action against harmful fungi are known from the literature (Code: SYP-Z048; EP-A 1 035 122).

The active compounds II, mentioned above as component 2, their preparation and their action against harmful fungi are generally known (cf.: http://www.hclrss.demon.co.uk/index.html); they are commercially available.

bitertanol, β-([1,1'-biphenyl]-4-yloxy)-α-(1,1-dimethylethyl)-1H-1,2,4-triazole-1-ethanol (DE 23 24 020), bromuconazole, 1-[[4-bromo-2-(2,4-dichlorophenyl)tetrahydro-2-furanyl]methyl]-1H-1,2,4-triazole (Proc. 1990 Br. Crop. Prot. Conf.—Pests Dis. Vol. 1, p. 459);

cyproconazole, 2-(4-chlorophenyl)-3-cyclopropyl-1-[1,2,4] triazol-1-ylbutan-2-ol (U.S. Pat. No. 4,664,696);

difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607);

diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575);

enilconazole (imazalil), 1-[2-(2,4-dichlorphenyl)-2-(2-propenyloxy)ethyl]-1H-imidazole (Fruits, 1973, Vol. 28, p. 545);

epoxiconazole, (2RS,3SR)-1-[3-(2-chlorophenyl)-2,3-epoxy-2-(4-fluorophenyl)propyl]-1H-1,2,4-triazole (EP-A 196 038);

fluquinconazole, 3-(2,4-dichlorophenyl)-6-fluoro-2-[1,2,4]-triazol-1-yl-3H-quinazolin-4-one (Proc. Br. Crop Prot. Conf.—Pests Dis., 5-3, 411 (1992));

fenbuconazole, α-[2-(4-chlorophenyl)ethyl]-α-phenyl-1H-1,2,4-triazole-1-propanenitrile (Proc. 1988 Br. Crop Prot. Conf.—Pests Dis. Vol. 1, p. 33);

flusilazole, 1-{[bis-(4-fluorophenyl)methylsilanyl]methyl}-1H-[1,2,4]triazole (Proc. Br. Crop Prot. Conf.—Pests Dis., 1, 413 (1984));

flutriafol, α-(2-fluorophenyl)-α-(4-fluorophenyl)-1H-1,2,4-triazole-1-ethanol (EP 15 756);

hexaconazole, 2-(2,4-dichlorophenyl)-1-[1,2,4]triazol-1-yl-hexan-2-ol (CAS RN 79983-71-4);

imibenconazole, (4-chlorophenyl)methyl N-(2,4-dichlorophenyl)-1H-1,2,4-triazole-1-ethanimidothioate ((Proc. 1988 Br. Crop Prot. Conf.—Pests Dis. Vol. 2, p. 519), imidothioate ((Proc. 1988 Br. Crop Prot. Conf.—Pests Dis. Vol. 2, p. 519), ipconazole, 2-[(4-chlorophenyl)methyl]-5-(1-methylethyl)-1-(1H-1,2,4-triazol-1-ylmethyl)cyclopentanol (EP 267 778), metconazole, 5-(4-chlorobenzyl)-2,2-dimethyl-1-[1,2,4]triazol-1-ylmethylcyclopentanol (GB 857 383);

myclobutanil, 2-(4-chlorophenyl)-2-[1,2,4]triazol-1-ylmethylpentanenitrile (CAS RN 88671-89-0);

penconazole, 1-[2-(2,4-dichlorophenyl)pentyl]-1H-[1,2,4] triazole (Pesticide Manual, 12th Ed. (2000), p. 712);

propiconazole, 1-[[2-(2,4-dichlorophenyl)-4-propyl-1,3-dioxolan-2-yl]methyl]-1H-1,2,4-triazole (BE 835 579);

prothioconazole, 2-[2-(1-chlorocyclopropyl)-3-(2-chlorophenyl)-2-hydroxypropyl]-2,4-dihydro-[1,2,4]triazole-3-thione (WO 96/16048);

simeconazole, α-(4-fluorophenyl)-α-[(trimethylsilyl)methyl]-1H-1,2,4-triazole-1-ethanol [CAS RN 149508-90-7], triadimefon, 1-(4-chlorophenoxy)-3,3-dimethyl-1-(1H-1,2,4-triazol-1-yl)-2-butanone;

triadimenol, β-(4-chlorophenoxy)-α-(1,1-dimethylethyl)-1H-1,2,4-triazole-1-ethanol;

tebuconazole, 1-(4-chlorophenyl)-4,4-dimethyl-3-[1,2,4] triazol-1-ylmethylpentan-3-ol (EP-A 40 345);

tetraconazole, 1-[2-(2,4-dichlorophenyl)-3-(1,1,2,2-tetrafluoroethoxy)propyl]-1H-1,2,4-triazole (EP 234 242);

triticonazole, (5E)-5-[(4-chlorophenyl)methylene]-2,22-dimethyl-1-(1H-1,2,4-triazol-1-ylmethyl)cyclopentanol (FR 26 41 277);

prochloraz, N-{propyl-[2-(2,4,6-trichlorophenoxy)ethyl] }imidazole-1-carboxamide (U.S. Pat. No. 3,991,071);

pefurazoate, 4-pentenyl 2-[(2-furanylmethyl)(1H-imidazol-1-ylcarbonyl)amino]butanoate [CAS RN 101903-30-4], triflumizole, (4-chloro-2-trifluoromethylphenyl)-(2-propoxy-1-[1,2,4]triazol-1-ylethylidene)amine (JP-A 79/119 462)

cyazofamid, 4-chloro-2-cyano-N,N-dimethyl-5-(4-methylphenyl)-1H-imidazole-1-sulfonamide [CAS RN 120116-88-3], benomyl, N-butyl-2-acetylaminobenzoimidazol-1-carboxamide (U.S. Pat. No. 3,631,176);

carbendazim, methyl (1H-benzoimidazol-2-yl)-carbamate (U.S. Pat. No. 3,657,443);

thiabendazole, 2-(1,3-thiazol-4-yl)benzimidazole (U.S. Pat. No. 3,017,415), fuberidazole, 2-(2-furanyl)-1H-benzimidazole (DE 12 09 799), ethaboxam, N-(cyano-2-thienylmethyl)-4-ethyl-2-(ethylamino)-5-thiazolcarboxamide (EP-A 639 574), etridiazole, hymexazole, 5-methyl-1,2-oxazol-3-ol (JP 518249, JP 532202), azoxystrobin, methyl 2-{2-[6-(2-cyano-1-vinylpenta-1,3-dienyloxy)pyrimidin-4-yloxy]phenyl}-3-methoxyacrylate (EP-A 382 375), dimoxystrobin, (E)-2-(methoxyimino)-N-methyl-2-[α-(2,5-xylyloxy)-o-tolyl]acetamide (EP-A 477 631);

fluoxastrobin, (E)-{2-[6-(2-chlorophenoxy)-5-fluoropyrimidin-4-yloxy]phenyl}(5,6-dihydro-1,4,2-dioxazin-3-yl) methanone O-methyloxime (WO 97/27189);

kresoxim-methyl, methyl (E)-methoxyimino[α-(o-tolyloxy)-o-tolyl]acetate (EP-A 253 213);

metominostrobin, (E)-2-(methoxyimino)-N-methyl-2-(2-phenoxyphenyl)acetamide (EP-A 398 692);

orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552);

picoxystrobin, methyl 3-methoxy-2-[2-(6-trifluoromethylpyridin-2-yloxymethyl)phenyl]-acrylate (EP-A 278 595);

pyraclostrobin, methyl N-{2-[1-(4-chlorophenyl)-1H-pyrazol-3-yloxymethyl]phenyl}(N-methoxy)carbamate (WO-A 96/01256);

trifloxystrobin, methyl (E)-methoxyimino-{(E)-α-[1-(α,α,α-trifluoro-m-tolyl)ethylidene-aminooxy]-o-tolyl}acetate (EP-A 460 575);

carboxin, 5,6-dihydro-2-methyl-N-phenyl-1,4-oxathiin-3-carboxamide (U.S. Pat. No. 3,249,499), benalaxyl, methyl N-(phenylacetyl)-N-(2,6-xylyl)-DL-alaninate (DE 29 03 612), boscalid, 2-chloro-N-(4'-chlorobiphenyl-2-yl)nicotinamide (EP-A 545 099);

fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327);

flutolanil, α,α,α-trifluoro-3'-isopropoxy-o-toluanilide (JP 1104514), furametpyr, 5-chloro-N-(1,3-dihydro-1,1,3-trimethyl-4-isobenzofuranyl)-1,3-dimethyl-1H-pyrazole-4-carboxamide [CAS RN 123572-88-3], mepronil, 3'-isopropoxy-o-toluanilide (U.S. Pat. No. 3,937,840), metalaxyl, methyl N-(methoxyacetyl)-N-(2,6-xylyl)-DL-alaninate (GB 15 00 581);

mefenoxam, methyl N-(2,6-dimethylphenyl)-N-(methoxyacetyl)-D-alaninate;

ofurace, (RS)-α-(2-chloro-N-(2,6-xylylacetamido)-γ-butyrolactone [CAS RN 58810-48-3];

oxadixyl; N-(2,6-dimethylphenyl)-2-methoxy-N-(2-oxo-3-oxazolidinyl)acetamide (GB 20 58 059), oxycarboxin, 5,6-dihydro-2-methyl-1,4-oxathiin-3-carboxanilide 4,4-dioxide (U.S. Pat. No. 3,399,214), penthiopyrad, N-[2-(1,3-dimethylbutyl)-3-thienyl]-1-methyl-3-(trifluoromethyl)-1H-pyrazole-4-carboxamide (JP 10130268), thifluzamide, N-[2,6-dibromo-4-(trifluoromethoxy)phenyl]-2-methyl-4-(trifluoromethyl)-5-thiazolecarboxamide;

tiadinil, 3'-chloro-4,4'-dimethyl-1,2,3-thiadiazole-5-carboxanilide [CAS RN 223580-51-6], dimethomorph, 3-(4-chlorophenyl)-3-(3,4-dimethoxyphenyl)-1-morpholin-4-ylpropenone (EP-A 120 321);

flumorph, 3-(4-fluorophenyl)-3-(3,4-dimethoxyphenyl)-1-morpholin-4-ylpropenone (EP-A 860 438);

flumetover, 2-(3,4-dimethoxyphenyl)-N-ethyl-α,α,α-trifluoro-N-methyl-p-toluamide [AGROW No. 243, 22 (1995)], fluopicolide (picobenzamid), 2,6-dichloro-N-(3-chloro-5-trifluoromethylpyridin-2-ylmethyl)benzamide (WO 99/42447);

zoxamide, (RS)-3,5-dichloro-N-(3-chloro-1-ethyl-1-methyl-2-oxopropyl)-p-toluamide [CAS RN 156052-68-5];

carpropamid, 2,2-dichloro-N-[1-(4-chlorophenyl)ethyl]-1-ethyl-3-methylcyclopropane-carboxamide [CAS RN 104030-54-8], diclocymet, 2-cyano-N-[(1R-1-(2,4-dichlorophenyl)ethyl]-3,3-dimethylbutanamide;

mandipropamid, (RS)-2-(4-chlorophenyl)-N-[3-methoxy-4-(prop-2-ynyloxy)phenethyl]-2-(prop-2-ynyloxy)acetamide [CAS RN 374726-62-2];

fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474);

pyrifenox, 1-(2,4-dichlorophenyl)-2-(3-pyridinyl)ethanone O-methyloxime (EP-A 49 854);

bupirimate, cyprodinil, (4-cyclopropyl-6-methylpyrimidin-2-yl)phenylamine (EP-A 310 550);

fenarimol, (4-chlorophenyl)(2-chlorophenyl)pyrimidin-5-ylmethanol (GB 12 18 623);

ferimzone, (Z)-2'-methylacetophenone 4,6-dimethylpyrimidin-2-ylhydrazone;

mepanipyrim, (4-methyl-6-prop-1-ynylpyrimidin-2-yl)phenylamine (EP-A 224 339);

nuarimol, α-(2-chlorophenyl)-α-(4-fluorophenyl)-5-pyrimidinemethanol (GB 12 18 623);

pyrimethanil, 4,6-dimethylpyrimidin-2-ylphenylamine (DD-A 151 404);

triforine, N,N'-{piperazine-1,4-diylbis[(trichloromethyl)methylene]}diformamide (DE 19 01 421);

fenpiclonil, 4-(2,3-dichlorophenyl)-1H-pyrrole-3-carbonitrile (Proc. 1988 Br. Crop Prot. Conf.—Pests Dis., Vol. 1, p. 65);

fludioxonil, 4-(2,2-difluorobenzo[1,3]dioxol-4-yl)-1H-pyrrole-3-carbonitrile (The Pesticide Manual, publ. The British Crop Protection Council, 10th ed. (1995), p. 482);

aldimorph, 4-alkyl-2,5(or 2,6)-dimethylmorpholine, comprising 65-75% of 2,6-dimethylmorpholine and 25-35% of 2,5-dimethylmorpholine, comprising more than 85% of 4-dodecyl-2,5(or 2,6)-dimethylmorpholine, where "alkyl" may also include octyl, decyl, tetradecyl and hexadecyl and where the cis/trans ratio is 1:1;

dodemorph, 4-cyclododecyl-2,6-dimethylmorpholine (DE 1198125);

fenpropimorph, (RS)-cis-4-[3-(4-tert-butylphenyl)-2-methylpropyl]-2,6-dimethylmorpholine (DE 27 52 096);

tridemorph, 2,6-dimethyl-4-tridecylmorpholine (DE 11 64 152);

fenpropidin, (RS)-1-[3-(4-tert-butylphenyl)-2-methylpropyl]piperidine (DE 27 52 096);

iprodione, N-isopropyl-3-(3,5-dichlorophenyl)-2,4-dioxoimidazolidine-1-carboxamide (GB 13 12 536);

procymidone, N-(3,5-dichlorophenyl)-1,2-dimethylcyclopropane-1,2-dicarboximide (U.S. Pat. No. 3,903,090);

vinclozolin, 3-(3,5-dichlorophenyl)-5-methyl-5-vinyloxazolidine-2,4-dione (DE-OS 22 07 576);

famoxadone, (RS)-3-anilino-5-methyl-5-(4-phenoxyphenyl)-1,3-oxazolidine-2,4-dione;

fenamidone, (S)-1-anilino-4-methyl-2-methylthio-4-phenylimidazolin-5-one;

octhilinone, probenazole, 3-allyloxy-1,2-benzothiazole 1,1-dioxide [CAS RN 27605-76-1]

anilazine, 4,6-dichloro-N-(2-chlorophenyl)-1,3,5-triazine-2-amine (U.S. Pat. No. 2,720,480);

diclomezine, 6-(3,5-dichlorophenyl)-p-tolyl)pyridazin-3 (2H)-one;

pyroquilone, 1,2,5,6-tetrahydropyrrolo[3,2,1-ij]quinolin-4-one (GB 13 94 373);

proquinazid, 6-iodo-2-propoxy-3-propylquinazolin-4(3H)-one (WO 97/48684);

tricyclazole, 5-methyl-1,2,4-triazolo[3,4-b]benzothiazole (GB 14 19 121);

acibenzolar-5-methyl, captafol, N-(1,1,2,2-tetrachloroethylthio)cyclohex-4-ene-1, 2-dicarboximide;

captan, 2-trichloromethylsulfanyl-3a,4,7,7a-tetrahydroisoindole-1,3-dione (U.S. Pat. No. 2,553,770);

dazomet, 3,5-dimethyl-1,3,5-thiadiazinane-2-thione;

folpet, 2-trichloromethylsulfanylisoindole-1,3-dione (U.S. Pat. No. 2,553,770);

fenoxanil, N-(1-cyano-1,2-dimethylpropyl)-2-(2,4-dichlorophenoxy)propanamide (EP-A 262 393);

quinoxyfen, 5,7-dichloro-4-(4-fluorophenoxy)quinoline (U.S. Pat. No. 5,240,940);

mancozeb, manganese ethylenebis(dithiocarbamate) zinc complex (U.S. Pat. No. 3,379,610);

maneb, manganese ethylenebis(dithiocarbamate) (U.S. Pat. No. 2,504,404);

metam, methyldithiocarbaminic acid (U.S. Pat. No. 2,791,605);

metiram, zinc ammoniate ethylenebis(dithiocarbamate) (U.S. Pat. No. 3,248,400);

propineb, zinc propylenebis(dithiocarbamate) polymer (BE 611 960);

ferbam, iron(3+) dimethyldithiocarbamate (U.S. Pat. No. 1,972,961);

thiram, bis(dimethylthiocarbamoyl) disulfide (DE 642 532);

ziram, dimethyldithiocarbamate;

zineb, zinc ethylenebis(dithiocarbamate) (U.S. Pat. No. 2,457,674);

diethofencarb, isopropyl 3,4-diethoxycarbanilate;

iprovalicarb, isopropyl [(1S)-2-methyl-1-(1-p-tolylethylcarbamoyl)propyl]carbamate (EP-A 472 996);

flubenthiavalicarb (benthiavalicarb), isopropyl {(S)-1-[(1R)-1-(6-fluorobenzothiazol-2-yl)ethylcarbamoyl]-2-methylpropyl}carbamate (JP-A 09/323,984);

propamocarb, propyl 3-(dimethylamino)propylcarbamate (DE 16 43 040);

dodine, (2,4-dichlorophenoxy)acetic acid (U.S. Pat. No. 2,867,562);
iminoctadine, guazatine, mixture comprising iminoctadine, bis(8-guanadinooctyl)amine (GB 11 14 155);
kasugamycin, 1L-1,3,4/2,5,6-1-deoxy-2,3,4,5,6-pentahydroxycyclohexyl 2-amino-2,3,4,6-tetradeoxy-4-(α-iminoglycino)-α-D-arabino-hexopyranozide;
streptomycin, O-2-deoxy-2-methylamino-α-L-glucopyranosyl-(1→2)-O-5-dioxy-3-C-formyl-α-L-lyxofuranosyl-(1→4)$N^1,N^3$-diamidino-D-streptamine;
polyoxins, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-β-D-allofuranuronic acid and the salts thereof;
validamycin A,
binapacryl, (RS)-2-sec-butyl-4,6-dinitrophenyl 3-methylcrotonate;
dinocap, the mixture of 2,6-dinitro-4-octylphenyl crotonate and 2,4-dinitro-6-octylphenyl crotonate, wherein "octyl" is a mixture of 1-methylheptyl, 1-ethylhexyl and 1-propylpentyl (U.S. Pat. No. 2,526,660);
dinobuton, (RS)-2-sec-butyl-4,6-dinitrophenyl isopropyl carbonate;
dithianon, 5,10-dioxo-5,10-dihydronaphtho[2,3-b][1,4]dithiin-2,3-dicarbonitrile (GB 857 383);
isoprothiolane, indol-3-ylacetic acid [CAS RN 50512-35-1];
fentin acetate, triphenyltin acetate;
edifenphos, O-ethyl S,S-diphenyl phosphonodithioate;
iprobenfos,
fosetyl, fosetyl aluminum, ethylphosphonate, aluminum salt (FR 22 54 276);
pyrazophos,
tolclofos-methyl,
chlorothalonil, 2,4,5,6-tetrachloroisophthalonitrile (U.S. Pat. No. 3,290,353);
dichlofluanid, N-dichlorofluoromethylthio-N',N'-dimethyl-N-phenylsulfamide (DE 11 93 498);
flusulfamide,
hexachlorobenzene,
phthalide,
pencycuron, 1-(4-chlorobenzyl)-1-cyclopentyl-3-phenylurea (DE 27 32 257);
quintozene, pentachloronitrobenzene (DE 682 048);
thiophanate-methyl, 1,2-phenylenebis(iminocarbonothioyl) bis(dimethylcarbamate) (DE-OS 19 30 540);
tolylfluanid, N-dichlorofluoromethylthio-N',N'-dimethyl-N-p-tolylsulfamide (DE 11 93 498);
cyflufenamid, (Z)—N-[α-(cyclopropylmethoxyimino)-2,3-difluoro-6-(trifluoromethyl)benzyl]-2-phenylacetamide (WO 96/19442);
cymoxanil, 1-(2-cyano-2-methoxyiminoacetyl)-3-ethylurea (U.S. Pat. No. 3,957,847);
dimethirimol,
ethirimol,
furalaxyl,
metrafenone, 3'-bromo-2,3,4,6'-tetramethoxy-2',6-dimethylbenzophenone (U.S. Pat. No. 5,945,567);
spiroxamine, (8-tert-butyl-1,4-dioxaspiro[4.5]dec-2-yl)diethylamine (EP-A 281 842).

The compounds named according to IUPAC, their preparation and their fungicidal action are likewise known:
5-chloro-7-(4-methylpiperidin-1-yl)-6-(2,4,6-trifluorophenyl)-[1,2,4]triazolo[1,5-a]pyrimidine (WO 98/46608),
3,4-dichloro-N-(2-cyanophenyl)isothiazole-5-carboxamide (WO 99/24413),
N-(2-{4-[3-(4-chlorophenyl)prop-2-ynyloxy]-3-methoxyphenyl}ethyl)-2-methanesulfonylamino-3-methylbutyramide (formula II-A), N-(2-{4-[3-(4-chlorophenyl)prop-2-ynyloxy]-3-methoxyphenyl}ethyl)-2-ethanesulfonylamino-3-methylbutyramide (formula II-B) (WO 04/049804),

II-A/II-B

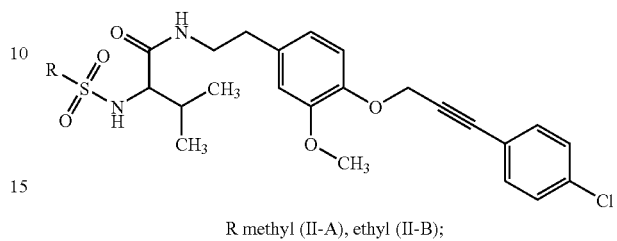

R methyl (II-A), ethyl (II-B);

amides of the formula III (WO 03/066609),
2-butoxy-6-iodo-3-propylchromen-4-one of the formula IV (WO 03/14103),

IV

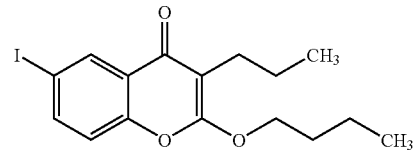

dimethyl-3-(3-bromo-6-fluoro-2-methylindole-1-sulfonyl)-[1,2,4]triazole-1-sulfonamide of the formula V (WO 03/053145),

V

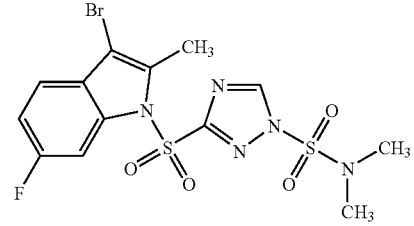

methyl 3-(4-chlorophenyl)-3-(2-isopropoxycarbonylamino-3-methylbutyrylamino)propanoate of the formula VI (EP-A 1028125),

VI

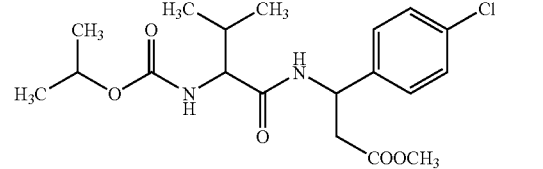

carbamate oxime ethers of the formula VII (EP-A 1201648).

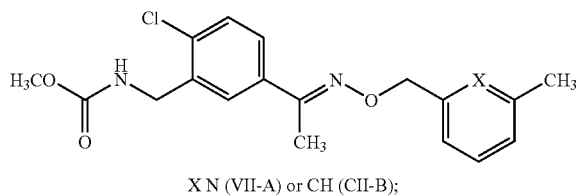

VII-A/VII-B

X N (VII-A) or CH (CII-B);

It is an object of the present invention, with a view to reducing the application rates and broadening the activity spectrum of the known compounds, to provide mixtures which, at a reduced total amount of active compounds applied, have improved activity against harmful fungi, in particular for certain indications.

We have found that this object is achieved by the mixtures defined at the outset. Moreover, we have found that simultaneous, that is joint or separate, application of the compound I and an active compound II or successive application of the compound I and an active compound II allows better control of harmful fungi than is possible with the individual compounds (synergistic mixtures). The compound I can be used as a synergist for a large number of different active compounds. The simultaneous, that is joint or separate, application of the compound I with an active compound II increases the fungicidal activity in a superadditive manner.

The mixtures of the compound I and an active compound II or the simultaneous, that is joint or separate, use of the compound I and an active compound II are distinguished by being highly active against a wide range of phytopathogenic fungi, in particular from the classes of the Ascomycetes, Deuteromycetes, Ooinycetes and Basidiomycetes. Some of them act systemically and can be used in crop protection as foliar- and soil-acting fungicides.

They are particularly important for controlling a multitude of fungi on various crop plants, such as bananas, cotton, vegetable species (for example cucumbers, beans and cucurbits), barley, grass, oats, coffee, potatoes, corn, fruit species, rice, rye, soybeans, tomatoes, grapevines, wheat, ornamental plants, sugar cane and on a large number of seeds.

They are advantageously suitable for the control of the following phytopathogenic fungi: *Blumeria graminis* (powdery mildew) on cereals, *Erysiphe cichoracearum* and *Sphaerotheca fuliginea* on cucurbits, *Podosphaera leucotricha* on apples, *Uncinula necator* on grapevines, *Puccinia* species on cereals, *Rhizoctonia* species on cotton, rice and lawns, *Ustilago* species on cereals and sugar cane, *Venturia inaequalis* on apples, *Bipolaris* and *Drechslera* species on cereals, rice and lawns, *Septoria* species on wheat, *Botrytis cinerea* on strawberries, vegetables, ornamental plants and grapevines, *Mycosphaerella* species on bananas, peanuts and cereals, *Pseudocercosporella herpotrichoides* on wheat and barley, *Pyricularia oryzae* on rice, *Phakopsora* species on soybeans, *Phytophthora infestans* on potatoes and tomatoes, *Pseudoperonospora* species on cucurbits and hops, *Plasmopara viticola* on grapevines, *Alternaria* species on fruit and vegetables and also *Fusarium* and *Verticillium* species.

The mixtures of the compound I and an active compound II are especially suitable for controlling *Botrytis* species.

The compound I and active compounds II can be applied simultaneously, that is jointly or separately, or in succession, the sequence, in the case of separate application, generally not having any effect on the result of the control measures.

In the definitions of the symbols given for formula III, collective terms were used which denote the following substituents:

halogen: fluorine, chlorine, bromine and iodine;

alkyl: saturated straight-chain or branched hydrocarbon radicals having 1 to 6 carbon atoms, for example $C_1$-$C_4$-alkyl, such as methyl, ethyl, propyl, 1-methylethyl, butyl, 1-methylpropyl, 2-methylpropyl, 1,1-dimethylethyl;

haloalkyl: straight-chain or branched alkyl groups having 1 to 6 carbon atoms, where some or all of the hydrogen atoms in these groups may be replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

With a view to the use of the amides of the formula III in the mixtures according to the invention, the following compounds of the formulae IIIa to IIIf are particularly suitable:

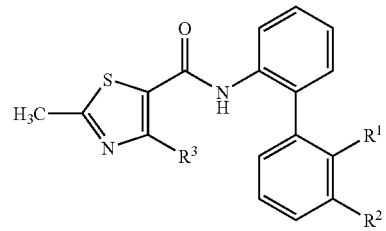

IIIa

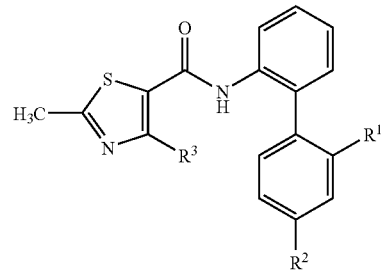

IIIb

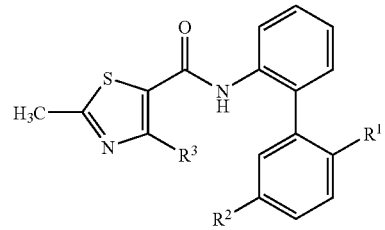

IIIc

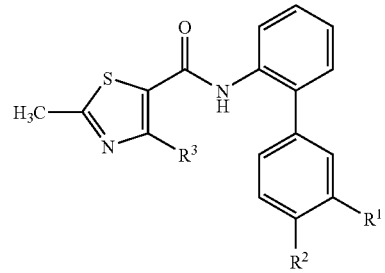

IIId

-continued

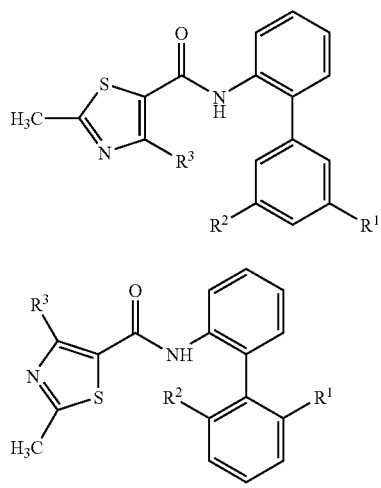

IIIe

IIIf

Among these, particular preference is given to the compounds of the formula IIId. Especially preferred are the compounds compiled in the tables below:

TABLE 1

Compound 1.1-1.22: compounds of the formula IIIa in which $R^1$ is fluorine and the combination of $R^2$ and $R^3$ is in each case one row of table A

TABLE 2

Compound 2.1-2.22: compounds of the formula IIIa in which $R^1$ is chlorine and the combination of $R^2$ and $R^3$ is in each case one row of table A

TABLE 3

Compound 3.1-3.22: compounds of the formula IIIa in which $R^1$ is bromine and the combination of $R^2$ and $R^3$ is in each case one row of table A

TABLE 4

Compound 4.1-4.22: compounds of the formula IIIa in which $R^1$ is iodine and the combination of $R^2$ and $R^3$ is in each case one row of table A

TABLE 5

Compound 5.1-5.22: compounds of the formula IIIa in which $R^1$ is methyl and the combination of $R^2$ and $R^3$ is in each case one row of table A

TABLE 6

Compound 6.1-6.22: compounds of the formula IIIa in which $R^1$ is methoxy and the combination of $R^2$ and $R^3$ is in each case one row of table A

TABLE 7

Compound 7.1-7.22: compounds of the formula IIIa in which $R^1$ is trifluoromethyl and the combination of $R^2$ and $R^3$ is in each case one row of table A

TABLE 8

Compound 8.1-8.22: compounds of the formula IIIa in which $R^1$ is trifluoromethoxy and the combination of $R^2$ and $R^3$ is in each case one row of table A

TABLE 9

Compound 9.1-9.22: compounds of the formula IIIa in which $R^1$ is cyano and the combination of $R^2$ and $R^3$ is in each case one row of table A

TABLE 10

Compound 10.1-10.22: compounds of the formula IIIa in which $R^1$ is nitro and $R^2$ is in each case one row of table A

TABLE 11

Compound 11.1-11.20: compounds of the formula IIIa in which $R^1$ is hydrogen and the combination of $R^2$ and $R^3$ is in each case one of rows 2 to 21 of table A

TABLE 12

Compound 12.1-12.22: compounds of the formula IIIb in which $R^1$ is fluorine and the combination of $R^2$ and $R^3$ is in each case one row of table A

TABLE 13

Compound 13.1-13.22: compounds of the formula IIIb in which $R^1$ is chlorine and the combination of $R^2$ and $R^3$ is in each case one row of table A

TABLE 14

Compound 14.1-14.22: compounds of the formula IIIb in which $R^1$ is bromine and the combination of $R^2$ and $R^3$ is in each case one row of table A

TABLE 15

Compound 15.1-15.22: compounds of the formula IIIb in which $R^1$ is iodine and the combination of $R^2$ and $R^3$ is in each case one row of table A

TABLE 16

Compound 16.1-16.22: compounds of the formula IIIb in which $R^1$ is methyl and the combination of $R^2$ and $R^3$ is in each case one row of table A

TABLE 17

Compound 17.1-17.22: compounds of the formula IIIb in which $R^1$ is methoxy and the combination of $R^2$ and $R^3$ is in each case one row of table A

TABLE 18

Compound 18.1-18.22: compounds of the formula IIIb in which $R^1$ is trifluoromethyl and the combination of $R^2$ and $R^3$ is in each case one row of table A

TABLE 19

Compound 19.1-19:22: compounds of the formula IIIb in which $R^1$ is trifluoromethoxy and the combination of $R^2$ and $R^3$ is in each case one row of table A

TABLE 20

Compound 20.1-20.22: compounds of the formula IIIb in which $R^1$ is cyano and the combination of $R^2$ and $R^3$ is in each case one row of table A

TABLE 21

Compound 21.1-21.22: compounds of the formula IIIb in which $R^1$ is nitro and the combination of $R^2$ and $R^3$ is in each case one row of table A

TABLE 22

Compound 22.1-22.20: compounds of the formula IIIb in which $R^1$ is hydrogen and the combination of $R^2$ and $R^3$ is in each case one of rows 2 to 21 of table A

TABLE 23

Compound 23.1-23.22: compounds of the formula IIIc in which $R^1$ is fluorine and the combination of $R^2$ and $R^3$ is in each case one row of table A

TABLE 24

Compound 24.1-24.22: compounds of the formula IIIc in which $R^1$ is chlorine and the combination of $R^2$ and $R^3$ is in each case one row of table A

TABLE 25

Compound 25.1-25.22: compounds of the formula IIIc in which $R^1$ is bromine and the combination of $R^2$ and $R^3$ is in each case one row of table A

TABLE 26

Compound 26.1-26.22: compounds of the formula IIIc in which $R^1$ is iodine and the combination of $R^2$ and $R^3$ is in each case one row of table A

TABLE 27

Compound 27.1-27.22: compounds of the formula IIIc in which $R^1$ is methyl and the combination of $R^2$ and $R^3$ is in each case one row of table A

TABLE 28

Compound 28.1-28.22: compounds of the formula IIIc in which $R^1$ is methoxy and the combination of $R^2$ and $R^3$ is in each case one row of table A

TABLE 29

Compound 29.1-29.22: compounds of the formula IIIc in which $R^1$ is trifluoromethyl and the combination of $R^2$ and $R^3$ is in each case one row of table A

TABLE 30

Compound 30.1-30.22: compounds of the formula IIIc in which $R^1$ is trifluoromethoxy and the combination of $R^2$ and $R^3$ is in each case one row of table A

TABLE 31

Compound 31.1-31.22: compounds of the formula IIIc in which $R^1$ is cyano and the combination of $R^2$ and $R^3$ is in each case one row of table A

TABLE 32

Compound 32.1-32.22: compounds of the formula IIIc in which $R^1$ is nitro and the combination of $R^2$ and $R^3$ is in each case one row of table A

TABLE 34

Compound 34.1-34.22: compounds of the formula IIId in which $R^1$ is fluorine and the combination of $R^2$ and $R^3$ is in each case one row of table A

TABLE 35

Compound 35.1-35.22: compounds of the formula IIId in which $R^1$ is chlorine and the combination of $R^2$ and $R^3$ is in each case one row of table A

TABLE 36

Compound 36.1-36.22: compounds of the formula IIId in which $R^1$ is bromine and the combination of $R^2$ and $R^3$ is in each case one row of table A

TABLE 37

Compound 37.1-37.22: compounds of the formula IIId in which $R^1$ is iodine and the combination of $R^2$ and $R^3$ is in each case one row of table A

TABLE 38

Compound 38.1-38.22: compounds of the formula IIId in which $R^1$ is methyl and the combination of $R^2$ and $R^3$ is in each case one row of table A

TABLE 39

Compound 39.1-39.22: compounds of the formula IIId in which $R^1$ is methoxy and the combination of $R^2$ and $R^3$ is in each case one row of table A

TABLE 40

Compound 40.1-40.22: compounds of the formula IIId in which $R^1$ is trifluoromethyl and the combination of $R^2$ and $R^3$ is in each case one row of table A

TABLE 41

Compound 41.1-41.22: compounds of the formula IIId in which $R^1$ is trifluoromethoxy and the combination of $R^2$ and $R^3$ is in each case one row of table A

TABLE 42

Compound 42.1-42.22: compounds of the formula IIId in which $R^1$ is cyano and the combination of $R^2$ and $R^3$ is in each case one row of table A

TABLE 43

Compound 43.1-43.22: compounds of the formula IIId in which $R^1$ is nitro and the combination of $R^2$ and $R^3$ is in each case one row of table A

TABLE 44

Compound 44.1-44.20: compounds of the formula IIId in which $R^1$ is hydrogen and the combination of $R^2$ and $R^3$ is in each case one of rows 2 to 21 of table A

TABLE 45

Compound 45.1-45.22: compounds of the formula IIIe in which $R^1$ is fluorine and the combination of $R^2$ and $R^3$ is in each case one row of table A

TABLE 46

Compound 46.1-46.22: compounds of the formula IIIe in which $R^1$ is chlorine and the combination of $R^2$ and $R^3$ is in each case one row of table A

TABLE 47

Compound 47.1-47.22: compounds of the formula IIIe in which $R^1$ is bromine and the combination of $R^2$ and $R^3$ is in each case one row of table A

TABLE 48

Compound 48.1-48.22: compounds of the formula IIIe in which $R^1$ is iodine and the combination of $R^2$ and $R^3$ is in each case one row of table A

TABLE 49

Compound 49.1-49.22: compounds of the formula IIIe in which $R^1$ is methyl and the combination of $R^2$ and $R^3$ is in each case one row of table A

TABLE 50

Compound 50.1-50.22: compounds of the formula IIIe in which $R^1$ is methoxy and the combination of $R^2$ and $R^3$ is in each case one row of table A

TABLE 51

Compound 51.1-51.22: compounds of the formula IIIe in which $R^1$ is trifluoromethyl and the combination of $R^2$ and $R^3$ is in each case one row of table A

TABLE 52

Compound 52.1-52.22: compounds of the formula IIIe in which $R^1$ is trifluoromethoxy and the combination of $R^2$ and $R^3$ is in each case one row of table A

TABLE 53

Compound 53.1-53.22: compounds of the formula IIIe in which $R^1$ is cyano and the combination of $R^2$ and $R^3$ is in each case one row of table A

TABLE 54

Compound 54.1-54.22: compounds of the formula IIIe in which $R^1$ is nitro and the combination of $R^2$ and $R^3$ is in each case one row of table A

TABLE 56

Compound 56.1-56.22: compounds of the formula IIIf in which $R^1$ is fluorine and the combination of $R^2$ and $R^3$ is in each case one row of table A

TABLE 57

Compound 57.1-57.22: compounds of the formula IIIf in which $R^1$ is chlorine and the combination of $R^2$ and $R^3$ is in each case one row of table A

TABLE 58

Compound 58.1-58.22: compounds of the formula IIIf in which $R^1$ is bromine and the combination of $R^2$ and $R^3$ is in each case one row of table A

TABLE 59

Compound 59.1-59.22: compounds of the formula IIIf in which $R^1$ is iodine and the combination of $R^2$ and $R^3$ is in each case one row of table A

TABLE 60

Compound 60.1-60.22: compounds of the formula IIIf in which $R^1$ is methyl and the combination of $R^2$ and $R^3$ is in each case one row of table A

TABLE 61

Compound 61.1-61.22: compounds of the formula IIIf in which $R^1$ is methoxy and the combination of $R^2$ and $R^3$ is in each case one row of table A

TABLE 62

Compound 62.1-62.22: compounds of the formula IIIf in which $R^1$ is trifluoromethyl and the combination of $R^2$ and $R^3$ is in each case one row of table A

TABLE 63

Compound 63.1-63.22: compounds of the formula IIIf in which $R^1$ is trifluoromethoxy and the combination of $R^2$ and $R^3$ is in each case one row of table A

TABLE 64

Compound 64.1-64.22: compounds of the formula IIIf in which $R^1$ is cyano and the combination of $R^2$ and $R^3$ is in each case one row of table A

TABLE 65

Compound 65.1-65.22: compounds of the formula IIIf in which $R^1$ is nitro and the combination of $R^2$ and $R^3$ is in each case one row of table A

TABLE 66

Compound 66.1-66.20: compounds of the formula IIIf in which $R^1$ is hydrogen and the combination of $R^2$ and $R^3$ is in each case one of rows 2 to 21 of table A

TABLE A

| No. | $R^2$ | $R^3$ |
| --- | --- | --- |
| 1 | H | $CF_3$ |
| 2 | F | $CF_3$ |
| 3 | Cl | $CF_3$ |
| 4 | Br | $CF_3$ |
| 5 | I | $CF_3$ |
| 6 | $CH_3$ | $CF_3$ |
| 7 | $OCH_3$ | $CF_3$ |
| 8 | $CF_3$ | $CF_3$ |
| 9 | $OCF_3$ | $CF_3$ |
| 10 | CN | $CF_3$ |
| 11 | $NO_2$ | $CF_3$ |
| 12 | F | $CHF_2$ |
| 13 | Cl | $CHF_2$ |
| 14 | Br | $CHF_2$ |
| 15 | I | $CHF_2$ |
| 16 | $CH_3$ | $CHF_2$ |
| 17 | $OCH_3$ | $CHF_2$ |
| 18 | $CF_3$ | $CHF_2$ |
| 19 | $OCF_3$ | $CHF_2$ |
| 20 | CN | $CHF_2$ |
| 21 | $NO_2$ | $CHF_2$ |
| 22 | H | $CHF_2$ |

The formula VII denotes compounds in which X is N (VII-A) or CH (VII-B).

A preferred embodiment of the mixtures according to the invention relates to the combination of the compound of the formula I and an active compound from the following groups:

dithiocarbamates, in particular mancozeb, propineb, thiram, benzimidazole, in particular benomyl, thiophanate, carbendazim, dicarboximides, in particular iprodione, procymidone, vinclozolin, chlozolinate, phthalimides, in particular captan, chlorothalonil, folpet, anilinopyrimidines, in particular cyprodinil, pyrimethanil, mepanipyrim, triazoles, in particular tebuconazole, difenoconazole, cyproconazole, myclobutanil, carboxanilides, in particular fenhexamid, benalaxyl, boscalid, penthiopyrad, an anilide of the formula III, the compound of the formula IV, organochlorine compounds, in particular dichlofluanid, chlorothalonil, tolyfluanid, carbamate, in particular diethofencarb, nitrogen-containing heterocyclyl compounds, in particular fludioxonil, fluazinam, strobilurins, in particular kresoxim-methyl, pyraclostrobin, azoxystrobin, trifloxystrobin, enestroburin, picoxystrobin, fluoxastrobin, organotin compounds, in particular, fentin-acetyl, and, in particular 5-chloro-7-(4-methylpiperidin-1-yl)-6-(2,4,6-trifluorophenyl)-[1,2,4]triazolo[1,5-a]pyrimidine.

When preparing the mixtures, it is preferred to employ the pure active compounds, to which further active compounds against harmful fungi or against other pests, such as insects, arachnids or nematodes, or else herbicidal or growth-regulating active compounds or fertilizers can be added as further active component according to need.

What is usually used are mixtures of the compound I with one active compound II. However, in certain cases, mixtures of the compound I with two or, if appropriate, a plurality of active components may be advantageous.

Suitable further active components in the above sense are in particular the active compounds II mentioned at the outset and especially the preferred active compounds mentioned above.

The compound I and the active compound II are usually applied in a weight ratio of from 100:1 to 1:100, preferably from 20:1 to 1:20, in particular from 10:1 to 1:10.

The further active components are, if desired, added in a ratio of from 20:1 to 1:20 to the compound I.

Depending on the type of compound and the desired effect, the application rates of the mixtures according to the invention are from 5 g/ha to 2000 g/ha, preferably from 50 to 900 g/ha, in particular from 50 to 750 g/ha.

Correspondingly, the application rates for the compound I are generally from 1 to 1000 g/ha, preferably from 10 to 900 g/ha, in particular from 20 to 750 g/ha.

Correspondingly, the application rates for the active compound II are generally from 1 to 2000 g/ha, preferably from 10 to 900 g/ha, in particular from 40 to 500 g/ha.

In the treatment of seed, application rates of mixture are generally from 1 to 1000 g/100 kg of seed, preferably from 1 to 750 g/100 kg, in particular from 5 to 500 g/100 kg.

The method for controlling harmful fungi is carried out by the separate or joint application of the compound I and the active compound II or of the mixtures of the compound I and the active compound II by spraying or dusting the seeds, the plants or the soil before or after sowing of the plants or before or after emergence of the plants.

The mixtures according to the invention, or the compound I and the active compound II, can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner, for example by extending the active compound with solvents and/or carriers, if desired using emulsifiers and dispersants. Solvents/auxiliaries suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable for use as surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum).

For the treatment of seed, the formulations in question give, after two- to ten-fold dilution, active compound concentrations of from 0.01 to 60% by weight, preferably from 0.1 to 40% by weight, in the ready-to-use preparations.

The following are examples of formulations of the invention:

1. Products for Dilution with Water

A Water-Soluble Concentrates (SL, LS)

10 parts by weight of the active compounds are dissolved with 90 parts by weight of water or a water-soluble solvent. As an alternative, wetters or other auxiliaries are added. The active compound dissolves upon dilution with water. In this way, a formulation having an active compound content of 10% by weight is obtained.

B Dispersible Concentrates (DC)

20 parts by weight of the active compounds are dissolved in 70 parts by weight of cyclohexanone with addition of 10 parts by weight of a dispersant, for example polyvinylpyrrolidone. Dilution with water gives a dispersion. The active compound content is 20% by weight C Emulsifiable Concentrates (EC)

15 parts by weight of the active compounds are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D Emulsions (EW, EO, ES)

25 parts by weight of the active compounds are dissolved in 35 parts by weight of xylene with addition of calcium dodecylbenzenesulfonate and castor oil ethoxylate (in each case 5 parts by weight). This mixture is added to 30 parts by weight of water by means of an emulsifying machine (for example Ultraturrax) and made into a homogeneous emulsion. Dilution with water gives an emulsion. The formulation has an active compound content of 25% by weight.

E Suspensions (SC, OD, FS)

In an agitated ball mill, 20 parts by weight of the active compounds are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules (WG, SG)

50 parts by weight of the active compounds are ground finely with addition of 50 parts by weight of dispersants and wetters and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders (WP, SP, SS, WS)

75 parts by weight of the active compounds are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a bead mill, 20 parts by weight of the active compounds, 10 parts by weight of dispersant, 1 part by weight of gelling agent and 70 parts by weight of water or an organic solvent are ground to give a fine suspension. Dilution with water gives a stable suspension having an active compound content of 20% by weight.

2. Products to be Applied Undiluted

I Dusts (DP, DS)

5 parts by weight of the active compounds are ground finely and mixed intimately with 95 parts by weight of finely divided kaolin. This gives a dustable product having an active compound content of 5% by weight.

J Granules (GR, FG, GG, MG)

0.5 part by weight of the active compounds is ground finely and associated with 99.5 parts by weight of carriers. Current methods are extrusion, spray-drying or the fluidized bed. This gives granules to be applied undiluted having an active compound content of 0.5% by weight.

K ULV Solutions (UL)

10 parts by weight of the active compounds are dissolved in 90 parts by weight of an organic solvent, for example xylene. This gives a product to be applied undiluted having an active compound content of 10% by weight.

For seed treatment, it is customary to employ water-soluble concentrates (LS), suspensions (FS), dusts (DS), water-dispersible and water-soluble powders (WS, SS), emulsions (ES), emulsifiable concentrates (EC) and gel formulations (GF). These formulations can be applied to the seed undiluted or, preferably, diluted. Application can be prior to sowing.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even to apply the active compound without additives.

Oils of various types, wetters, adjuvants, herbicides, fungicides, other pesticides, or bactericides may be added to the active compounds even, if appropriate, not until immediately prior to use (tank mix). These agents are typically admixed with the compositions according to the invention in a weight ratio of from 1:100 to 100:1, preferably from 1:10 to 10:1.

Suitable adjuvants in this context are in particular: organically modified polysiloxanes, for example Break Thru S 240®; alcohol alkoxylates, for example Atplus 245®, Atplus MBA 1303®, Plurafac LF 300® and Lutensol ON 30®; EO/PO block polymers, for example Pluronic RPE 2035® and Genapol B®; alcohol ethoxylates, for example Lutensol XP 80®; and sodium dioctylsulfosuccinate, for example Leophen RA®.

The compounds I and II or the mixtures or the corresponding formulations are applied by treating the harmful fungi, the plants, seeds, soils, areas, materials or spaces to be kept free from them with a fungicidally effective amount of the mixture or, in the case of separate application, of the compounds I and II. Application can be carried out before or after infection by the harmful fungi.

The fungicidal effect of the compound and the mixtures can be demonstrated by the following tests:

The active compounds were prepared jointly or separately as a stock solution with 25 mg of active compound which was made up to 10 ml using a mixture of acetone and/or DMSO and the emulsifier Uniperol® EL (wetting agent having emulsifying and dispersing action based on ethoxylated alkylphenols) in a volume ratio of solvent/emulsifier of 99 to 1. The mixture was then made up with water to 100 ml. This stock solution was diluted with the solvent/emulsifier/water mixture described to the concentration of active compounds stated below.

The active compounds epoxiconazole and pyraclostrobin were used as commercial formulations and diluted with water to the stated concentration.

The visually determined percentages of infected leaf areas were converted into efficacies in % of the untreated control:

The efficacy (E) is calculated as follows using Abbot's formula:

$$E = (1 - \alpha/\beta) \cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of mixtures of active compounds were determined using Colby's formula (Colby, S. R. "Calculating synergistic and antagonistic responses of herbicide combinations", Weeds, 15, 1967, p. 20-22) and compared with the observed efficacies.

Colby's formula:

$$E = x + y - x \cdot y/100$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b Use example 1—activity against gray mold on bell pepper leaves caused by *Botrytis cinerea*, 1 day protective application Bell pepper seedlings of the cultivar "Neusiedler Ideal Elite" were, after 2-3 leaves were well developed, sprayed to runoff point with an aqueous suspension having the active compound concentration given below. The next day, the treated plants were inoculated with a spore suspension of *Botrytis cinerea* which comprised $1.7 \times 10^6$ spores/ml in a 2% strength biomalt solution. The test plants were then placed in a dark climatized chamber at 22 to 24° C. and high atmospheric humidity. After 5 days, the extent of the fungal infection on the leaves could be determined visually in %.

| No. | Active compound | Conc. [ppm] | Ratio | Observed activity (%) | Activity calculated according to Colby (%) |
|---|---|---|---|---|---|
| 1 | — (control) | — | | 0 (100% infection) | |
| 2 | SYP-Z048 (I) | 4 | | 70 | |
| 3 | epoxiconazole (A7) | 4 | | 0 | |
| 4 | I + A7 | 4 + 4 | 1:1 | 90 | 70 |

Use example 2-activity against gray mold on bell pepper leaves caused by *Botrytis cinerea*, 5 day protective application Bell pepper seedlings of the cultivar "Neusiedler Ideal Elite" were, after 2-3 leaves were well developed, sprayed to runoff point with an aqueous suspension having the active compound concentration given below. After 5 days, the treated plants were inoculated with a spore suspension of *Botrytis cinerea* which comprised $1.7 \times 10^6$ spores/ml in a 2% strength aqueous biomalt solution. The test plants were then placed in a dark climatized chamber at 22 to 24° C. and high atmospheric humidity. After 5 days, the extent of the fungal infection on the leaves could be determined visually in %.

| No. | Active compound | Conc. [ppm] | Ratio | Observed activity (%) | Activity calculated according to Colby (%) |
|---|---|---|---|---|---|
| 5 | — (control) | — | | 0 (90% infection) | |
| 6 | SYP-Z048 (I) | 16 | | 0 | |
| 7 | pyraclostrobin (B9) | 63 | | 20 | |
| 8 | boscalid (C3) | 4 | | 0 | |
| 9 | tolylfluanid (F29) | 250 | | 20 | |
| 10 | I + B9 | 16 + 63 | 1:4 | 60 | 20 |
| 11 | I + C3 | 16 + 4 | 4:1 | 40 | 0 |
| 12 | I + F29 | 16 + 250 | 1:16 | 70 | 20 |

Use example 3-5 day protective activity against early blight of tomato caused by *Alternaria solani*

Leaves of potted plants of the cultivar "Goldene Königin" were sprayed to runoff point with an aqueous suspension having the active compound concentration given below. After 5 days, the leaves were infected with an aqueous spore suspension of *Alternaria solani* in a 2% biomalt solution having a density of $0.17 \times 10^6$ spores/ml. The plants were then placed in a water vapor-saturated chamber at temperatures between 20 and 22° C. After 5 days, the disease on the untreated but infected control plants had developed to such an extent that the infection could be determined visually in %.

| No. | Active compound | Conc. [ppm] | Ratio | Observed activity (%) | Activity calculated according to Colby (%) |
|---|---|---|---|---|---|
| 13 | — (control) | — | | 0 (90% infection) | |
| 14 | SYP-Z048 (I) | 1 | | 0 | |
| 15 | boscalid (C3) | 4 | | 56 | |
| 16 | I + C3 | 1 + 4 | 1:4 | 72 | 56 |

The test results show that, by virtue of the synergism, the mixtures according to the invention are considerably more active than had been predicted using Colby's formula.

We claim:

1. A fungicidal mixture for controlling phytopathogenic harmful fungi, which mixture comprises two active components:

1) the isoxazole derivative of the formula I,

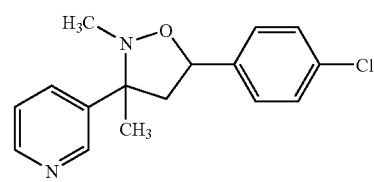

I and 2) at least one active compound II selected from the group consisting of epoxiconazole, pyraclostrobin, boscalid, amides of the formula III:

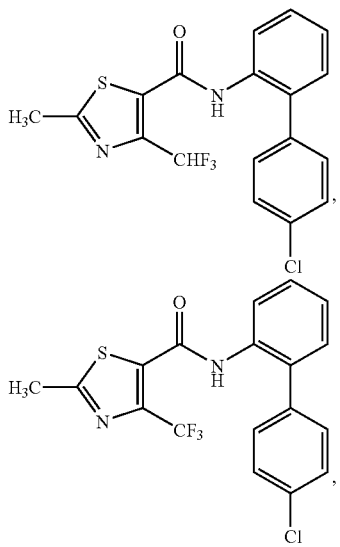

fenpropimorph, mancozeb, zineb, dithianon, tolylfluanid and spiroxamine in a synergistically effective amount.

2. The fungicidal mixture according to claim 1 which comprises the compound of the formula I and the compound of the formula II in a weight ratio of from 100:1 to 1:100.

3. The fungicidal mixtures according to claim 1 further comprising a liquid or solid carrier.

4. A method for controlling phytopathogenic harmful fungi which comprises contacting the fungi, their habitat or the seed, the soil or the plants to be protected against fungal attack with an effective amount of the compound I and the compound II according to claim 1.

5. The method according to claim 4, wherein the compounds I and II are applied simultaneously, that is jointly or separately, or in succession.

6. The method according to claim 4, wherein the compounds I and II are applied in an amount of from 5 g/ha to 2000 g/ha.

7. The method according to claim 4, wherein the compounds I and II are applied in an amount of from 1 to 1000 g/100 kg of seed.

8. Seed treated with the mixture according to claim 1 in an amount of from 1 to 1000 g/100 kg.

9. The fungicidal mixture of claim 2, wherein said at least one active compound II is epoxiconazole.

10. The fungicidal mixture of claim 2, wherein said at least one active compound II is pyraclostrobin.

11. The fungicidal mixture of claim 2, wherein said at least one active compound II is boscalid.

12. The fungicidal mixture of claim 2, wherein said at least one active compound II is tolylfluanid.

13. The fiingicidal mixture of claim 1, wherein said at least one active compound II is dithianon.

14. The fungicidal mixture of claim 1, wherein said at least one active compound II is spiroxamine.

15. The fungicidal mixture of claim 1, wherein said at least one active compound II is mancozeb.

16. The fungicidal mixture of claim 1, wherein said at least one active compound II is zineb.

17. The fungicidal mixture of claim 1, wherein said at least one active compound II is fenpropimorph.

18. The fungicidal mixture of claim 1, wherein said at least one active compound II is an amide of formula III,

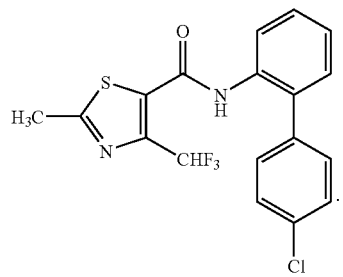

19. The fungicidal mixture of claim 1, wherein said at least one active compound II is an amide of formula III,

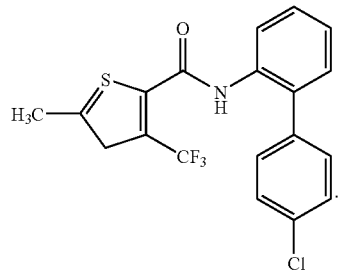

* * * * *

UNITED STATES PATENT AND TRADEMARK OFFICE
CERTIFICATE OF CORRECTION

PATENT NO. : 7,598,206 B2  Page 1 of 3
APPLICATION NO. : 11/793899
DATED : October 6, 2009
INVENTOR(S) : Markus Gewehr et al.

It is certified that error appears in the above-identified patent and that said Letters Patent is hereby corrected as shown below:

Col. 25, in claim 1, lines 1-12, the formula
"

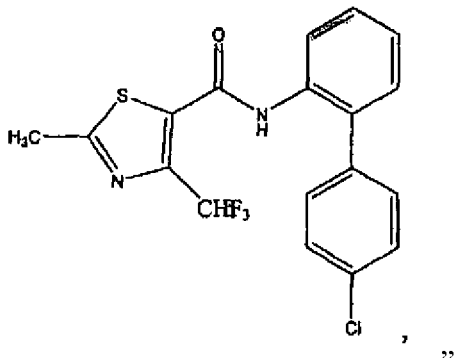

,"

should be
--

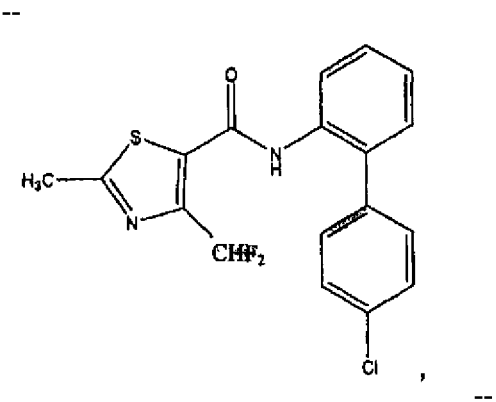

, --

Col. 26, claim 13, line 7, "flingicidal", should be --fungicidal--;

UNITED STATES PATENT AND TRADEMARK OFFICE
CERTIFICATE OF CORRECTION

PATENT NO. : 7,598,206 B2  
APPLICATION NO. : 11/793899  
DATED : October 6, 2009  
INVENTOR(S) : Markus Gewehr et al.

Page 2 of 3

It is certified that error appears in the above-identified patent and that said Letters Patent is hereby corrected as shown below:

Col. 26, in claim 18, lines 20-30, the formula
"

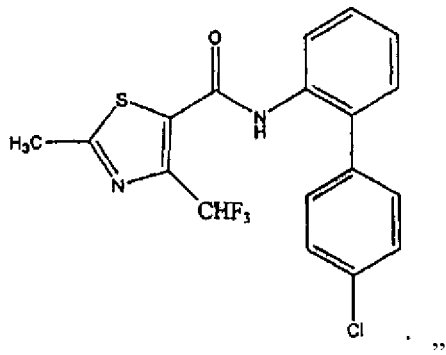

should be
--

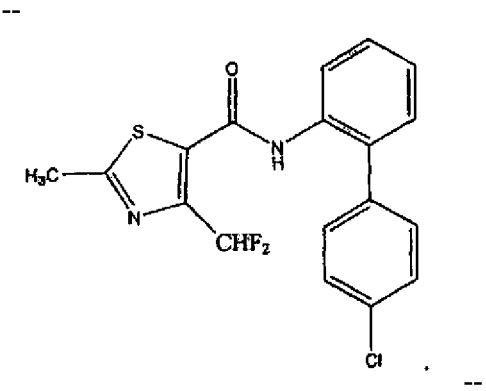

. --

UNITED STATES PATENT AND TRADEMARK OFFICE
CERTIFICATE OF CORRECTION

PATENT NO. : 7,598,206 B2
APPLICATION NO. : 11/793899
DATED : October 6, 2009
INVENTOR(S) : Markus Gewehr et al.

It is certified that error appears in the above-identified patent and that said Letters Patent is hereby corrected as shown below:

Col. 26, in claim 19, lines 35-45, the formula
"

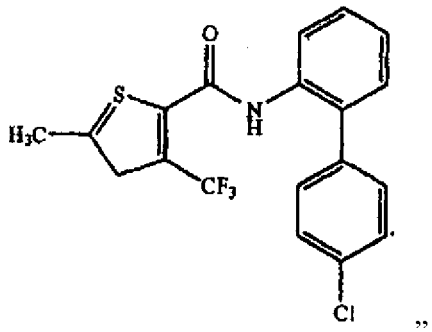

"

should be
--

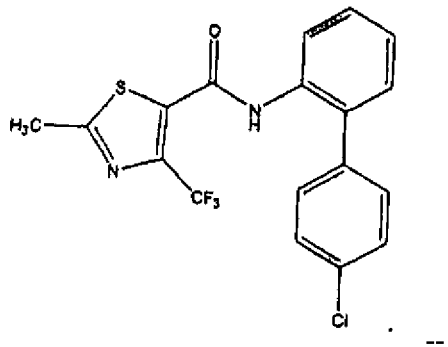

. --

Signed and Sealed this

Twenty-second Day of December, 2009

David J. Kappos
*Director of the United States Patent and Trademark Office*